United States Patent [19]

Frenzel

[11] 3,965,491

[45] June 29, 1976

[54] PROSTHETIC DEVICE FOR HOLDING GOLF CLUBS

[76] Inventor: William K. Frenzel, 151 Rte. 206, Bldg. 8, Apt. 3, Flanders, N.J. 07836

[22] Filed: Jan. 7, 1976

[21] Appl. No.: 647,058

[52] U.S. Cl. .................................................. 3/12.8
[51] Int. Cl.² ........................................... A61F 1/06
[58] Field of Search ............................... 3/12–12.8

[56] References Cited
UNITED STATES PATENTS

| | | | |
|---|---|---|---|
| 2,030,785 | 2/1936 | Dorrance | 3/12.8 |
| 3,747,128 | 7/1973 | DeFilipo | 3/12.8 |

FOREIGN PATENTS OR APPLICATIONS

| | | | |
|---|---|---|---|
| 541,425 | 5/1922 | France | 3/12.8 |

*Primary Examiner*—Ronald L. Frinks

[57] ABSTRACT

A base coupling member includes a pivotable control lever and a threaded shaft detachably secured to a prosthetic arm device. A pair of tapered semi-cylindrical tubular sleeves extend from the base and are adapted to receive and engage a handle of a club. The lever and a resilient band control the opening and closing of the two half sleeves to permit insertion and gripping of a standard golf club handle. A locking arm and bar at the ends of the opposite sleeves are coupled together to clamp the club in a fixed position.

8 Claims, 2 Drawing Figures

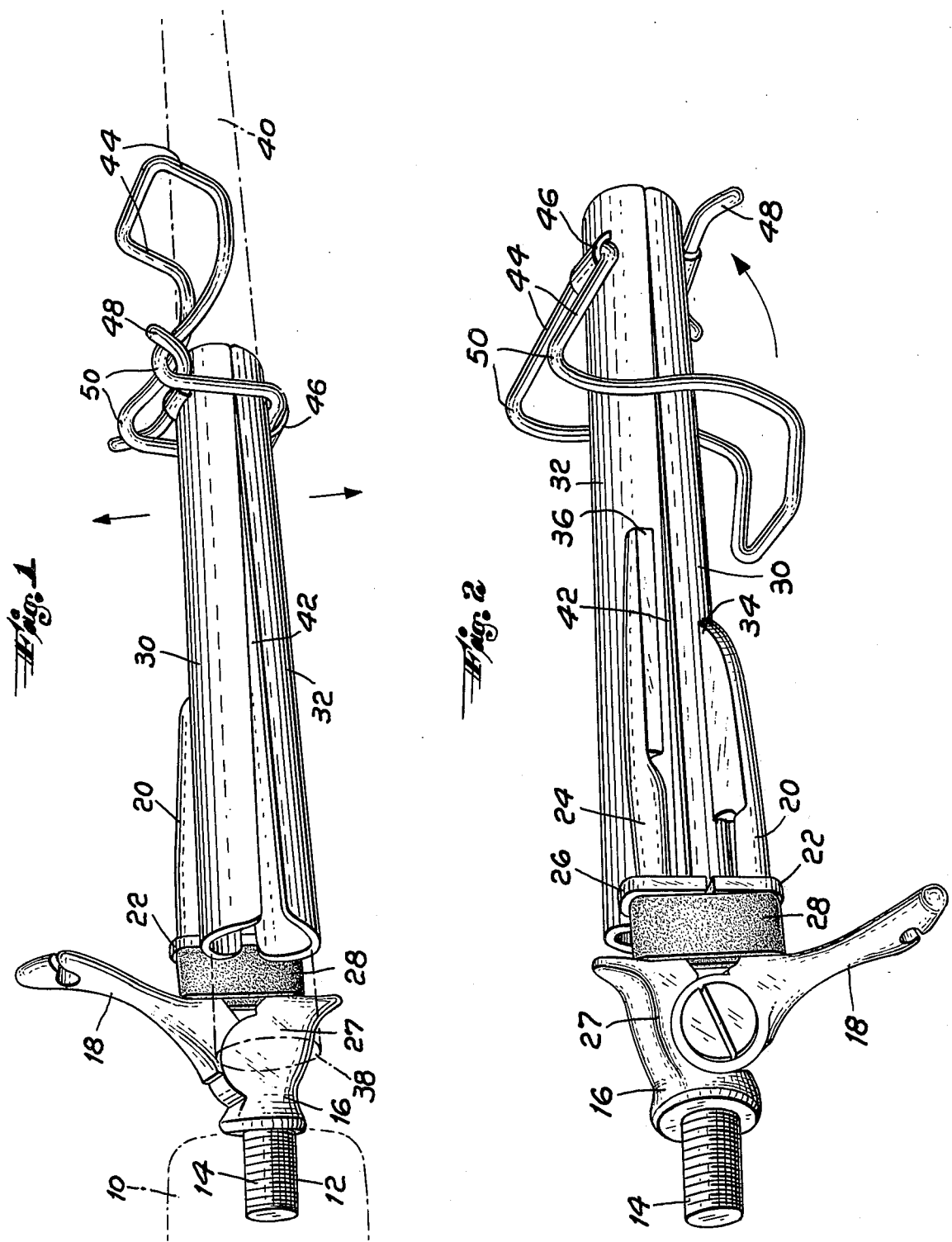

PROSTHETIC DEVICE FOR HOLDING GOLF CLUBS

BACKGROUND OF THE INVENTION

1. Field of the Invention

The present invention relates to an attachment for an artificial arm and particularly to a prosthetic device for holding golf clubs and the like.

2. Description of the Prior Art

Various attachments are available to permit amputees to use artificial arms for different purposes. Typical artificial hand devices are shown in U.S. Pat. No. 1,042,413, issued Oct. 29, 1912, and U.S. Pat. No. 2,030,785, issued Feb. 11, 1936, both to D. W. Dorrance. Such devices use a base having a threaded shaft which screws into a prosthetic arm socket. A pair of pivotable hooks extend from the base and are controlled by a lever connected to a shoulder piece by a cable. A resilient band holds the hooks in a normally closed position and movement of the cable and lever opens the hooks to permit grasping an article. This device is known in the art as a standard Dorrance hook which fits into a standard prosthetic arm.

Another attachment, particularly adapted for holding golf clubs, is shown in U.S. Pat. No. 3,747,128, issued July 24, 1973. This device includes a complex rotary link and a pair of clamp leaves which are secured around a club by a band clamp. The leaves are not connected or controlled by a standard lever and cable mechanism and are difficult to manipulate and tighten in a fixed position around a club.

SUMMARY OF THE INVENTION

It is therefore the primary object of the present invention to provide a simplified improved device for attachment to an artificial arm which will permit gripping a handle of a club in a secure controllable manner.

A further object is to provide a golf club holding device which will fit into a standard prosthetic arm and permit control by a standard hook type lever mechanism. This is achieved with a pair of longitudinally extending tapered semicylindrical tubular sleeves which are secured to a base support having a standard pivotable hook type lever mechanism and threaded shaft. The base is attached to a standard prosthetic arm socket. Movement of the lever opens the sleeves to permit engagement with the handle of a standard club inserted therein. A resilient band maintains the sleeves in a normally closed position to grip the club. A pivotable locking arm and fixed bar at the ends of the opposite sleeves are engaged to clamp the club in a stationary position. Other objects and advantages will become apparent from the following description in conjunction with the accompanying drawings.

BRIEF DESCRIPTION OF THE DRAWINGS

FIG. 1 is a pictorial side view of the prosthetic arm attachment showing a club handle in a locked position; and FIG. 2 is a view of the device from the opposite side showing a closed unlocked position.

DESCRIPTION OF THE PREFERRED EMBODIMENT

As shown in FIGS. 1 and 2, an artificial arm socket member 10, indicated by dashed lines, forms a portion of a standard unit attached to the upper arm and shoulder of an amputee. The socket member includes a threaded hole 12 which receives a threaded shaft 14 forming part of a metal base coupling member 16. Base 16 includes a pivotable control lever 18 which is operated by a cable, not shown, attached to the shoulder piece. Extending from and connected to the lever is a hook or support member 20 having a rim 22. A second hook support member 24 and rim 26 are connected to and extend from the fixed mounting portion 27 of base 16. Surrounding the base between the control lever 18 and the rims 22, 26 of support members 20, 24 is a heavy resilient elastic band 28, preferably of a thick strong rubber. Band 28 normally urges the support members and lever to maintain a closed stationary position. When lever 18 is operated by the cable, it opens the support members against the force of the band. The base member, control lever, shaft, band and extending hook supports are all known elements included in the standard attachment for the arm socket member.

Secured to the respective support members 20, 24 are a pair of longitudinally extending tapered semicylindrical tubular metal sleeve sections 30, 32. The sleeves are rigidly attached to the support members, preferably by welded joints 34, 36 or other suitable methods. A peripheral area at the base ends of the sleeves may also be directly welded to the shoulder portions 22, 26. The tapered sleeve halves are adapted to receive and engage a like-tapered handle 38 of a standard golf club 40 shown by dashed lines, or a similar device. When the control lever 18 is operated, the sleeves open and spread apart, as indicated by the arrows in FIG. 1, along a longitudinal tapered opening or split 42 between the edges of the abutting sections, so that the club handle can readily be inserted. Release of the lever then causes the resilient band 28 to close the sleeves about the handle and provide a firm grip. The sleeves are laterally offset with respect to the base 16 and lever 18 so that the end of the handle of the club can extend out of the ends of the split tubular sleeves alongside the base, as shown in FIG. 1. This permits gripping the club handle at any selected section along the length to suit the needs of any individual and to accommodate various sized clubs.

Disposed at the outer narrow end of one of the tapered sleeve halves 32 is a metal locking arm 44 pivotably secured at the ends in a laterally extending metal loop 46. The corresponding outer narrow end of the opposite sleeve half 30 includes a laterally extending curved metal locking bar 48. In the unlocked position, as shown in FIG. 2, arm 44 hangs loosely over the sleeves toward the base end. When a club handle is inserted into and engaged by the sleeves, the arm is pivoted toward the narrow end, as indicated by the arrow. As shown in FIG. 1, a bent elbow portion 50 of the arm engages the curved locking bar 48 to lock the sleeves together about the handle and hold the club in a fixed position. The looped end of the arm also provides a convenient grasping mechanism which facilitates the locking action as well as the disengagement of a club from sleeves.

The present device thus provides a simple secure attachment to a prosthetic arm which permits an amputee to hold and readily manipulate a standard golf club. While only a single embodiment has been illustrated and described, it is apparent that many variations may be made in the particular design and configuration without departing from the scope of the invention as set forth in the appended claims.

What is claimed is:

1. A prosthetic arm device comprising:
   a base member adapted to be coupled to a prosthetic arm socket member, said base member including a mounting member, a shaft extending from said mounting member and adapted to be detachably secured to said arm socket member, a control lever pivotably secured to said mounting member, a pair of adjacent support members extending respectively from said control lever and said mounting member, and resilient means urging said control lever and said support members to maintain a closed position;
   a pair of tapered tubular sleeve sections secured to and extending longitudinally from respective said support members, said control member being adapted to open said sleeves against the force of said resilient means to receive a handle of a club therebetween, said sleeves being adapted to engage said handle upon return to said closed position; and
   locking means on said sleeves to fixedly clamp said sleeve sections together around said handle.

2. The device of claim 1 wherein said shaft is threaded to engage a hole in said arm socket member.

3. The device of claim 2 wherein said sleeve sections are laterally offset from said base to permit an end of a club handle to extend out of the end of said sleeve sections alongside said base.

4. The device of claim 3 wherein said resilient means is an elastic band around said control member and mounting member.

5. The device of claim 4 wherein said locking means includes a locking arm pivotably secured to one of said sleeve sections and a locking bar extending laterally on the other said sleeve section, said locking arm engaging said locking bar to secure said arm and bar together.

6. The device of claim 5 wherein said tapered tubular sleeve sections are semicylindrical split halves having longitudinal abutting edges.

7. The device of claim 6 wherein said support members include lateral rims adjacent one edge of said elastic band.

8. The device of claim 7 wherein said support members extend alongside and are secured to the respective outer sides of said sleeves.

* * * * *